US010196318B2

(12) United States Patent
Werner

(10) Patent No.: US 10,196,318 B2
(45) Date of Patent: Feb. 5, 2019

(54) MICRONUTRIENT COMPOSITIONS

(71) Applicant: CRODA INTERNATIONAL PLC, Yorkshire (GB)

(72) Inventor: Márcia Fernanda Hergert Pereira Werner, São Paulo (BR)

(73) Assignee: Croda International Plc, East Yorkshire (GB)

( * ) Notice: Subject to any disclaimer, the term of this patent is extended or adjusted under 35 U.S.C. 154(b) by 0 days.

(21) Appl. No.: 15/121,281

(22) PCT Filed: Feb. 23, 2015

(86) PCT No.: PCT/GB2015/050507
§ 371 (c)(1),
(2) Date: Aug. 24, 2016

(87) PCT Pub. No.: WO2015/128620
PCT Pub. Date: Sep. 3, 2015

(65) Prior Publication Data
US 2017/0008813 A1   Jan. 12, 2017

(30) Foreign Application Priority Data
Feb. 28, 2014  (GB) .................................. 1403599.2

(51) Int. Cl.
  A01N 25/04    (2006.01)
  A01N 57/20    (2006.01)
  C05D 9/02     (2006.01)
  C05G 3/00     (2006.01)
  C05G 3/02     (2006.01)
  C05G 3/06     (2006.01)

(52) U.S. Cl.
  CPC .............. C05D 9/02 (2013.01); A01N 25/04 (2013.01); A01N 57/20 (2013.01); C05G 3/0076 (2013.01); C05G 3/02 (2013.01); C05G 3/06 (2013.01)

(58) Field of Classification Search
None
See application file for complete search history.

(56) References Cited

U.S. PATENT DOCUMENTS

2003/0161856 A1* 8/2003 Tandt ..................... A01N 25/04
424/405

FOREIGN PATENT DOCUMENTS

| BR | 201107333 | * | 11/2013 |
| CN | 101805547 | * | 8/2010 |
| CN | 102344640 | * | 2/2012 |
| CN | 102344640 A | * | 2/2012 |
| CN | 103304969 | * | 9/2013 |
| CN | 103360149 | * | 10/2013 |
| CN | 103360149 A | * | 10/2013 |
| CN | 103539560 | * | 1/2014 |
| CN | 103539560 A | * | 1/2014 |
| CN | 103621555 A | * | 3/2014 |
| EP | 697422 A1 | | 2/1996 |
| JP | 2006262723 A | * | 10/2006 |
| JP | 2013067921 | * | 4/2013 |
| KR | 218549 | * | 9/1999 |
| KR | 866588 | * | 11/2008 |
| KR | 866588 A | * | 11/2008 |
| WO | 9400508 A1 | | 1/1994 |
| WO | 9616930 A1 | | 6/1996 |
| WO | 03070705 A1 | | 8/2003 |
| WO | 2004016088 A2 | | 2/2004 |
| WO | 2011043660 A2 | | 4/2011 |
| WO | 2013093578 A1 | | 6/2013 |

OTHER PUBLICATIONS

International Search Report for PCT/GB2015/050507 (WO2015/128620), dated Apr. 17, 2015.

* cited by examiner

*Primary Examiner* — Alton N Pryor
(74) *Attorney, Agent, or Firm* — RatnerPrestia

(57) ABSTRACT

An agrochemical micronutrient concentrate and or formulations with dispersants for said concentrates/formulations, in particular a dispersant for use in suspending solid micronutrients in suspension concentrate type formulations comprising one or more micronutrients. The dispersant is preferably a water dispersible styrene (meth)acrylic copolymer. The micronutrient is selected from zinc oxide, manganese carbonate, manganese oxide, or calcium carbonate, and present in the concentrate at 40 wt. %. or more. The present invention also includes methods of treating crops with such micronutrient formulations.

18 Claims, No Drawings

MICRONUTRIENT COMPOSITIONS

CROSS REFERENCE TO RELATED APPLICATIONS

This application is the National Stage filing of international Appln. No. PCT/GB2015/050507, filed 23 Feb. 2015, and claims priority of GB Application No. 1403599.2, filed 28 Feb. 2014, the entirety of which applications is incorporated herein by reference for all purposes.

The present invention relates to agrochemical micronutrient concentrates/formulations and dispersants for said concentrates/formulations, in particular dispersants for use in said concentrates/formulations for suspending solid micronutrients in suspension concentrate type formulations comprising one or more micronutrients. The present invention also includes methods of treating crops with such formulations.

Agrochemical formulations are commonly supplied to the end user as a concentrate which is then diluted for use. Agrochemical actives and micronutrients can be added in the tank mix at the point of dilution. However, the concentrate itself may comprise all the required components so that only simple dilution is required before in treating crops.

Solid micronutrients in particular may be insoluble or only partly soluble in water, therefore this makes it difficult to supply concentrate comprising the micronutrient. Additionally, the typical inclusion rate of micronutrients in concentrates may be low, less than 20 wt. % of the micronutrient salt. The concentrates are accordingly very bulky.

Additionally, it has been found that use of higher amounts of micronutrients in a concentrate can result in instability in the dilute tank mix both before and after an agrochemical active is added. The tank mix may suffer from undesired coalescence/flocculation.

The present invention seeks to provide stable micronutrient concentrates including dispersants, where said dispersants are able to overcome the above described problems. Additionally, the present invention seeks to provide dispersants which have desired properties of a stable dispersion and suspension of the solid micronutrients in the concentrate suspension and in a diluted concentrate.

The present invention also provides for the use of the dispersants in agrochemical compositions formed by dilution of the concentrate and in combination with an agrochemical active. The present invention also seeks to provide the use of dilute concentrates comprising said dispersants for treatment of crops.

According to a first aspect of the present invention there is provided an agrochemical concentrate comprising;
   i) at least one micronutrient;
   ii) a dispersant, said dispersant being a styrene (meth) acrylic copolymer.

According to a second aspect of the present invention there is provided a method of preparing an agrochemical concentrate according to the first aspect, said method comprising mixing;
   at least one micronutrient;
   a dispersant, said dispersant being a styrene (meth)acrylic copolymer.

According to a third aspect of the present invention there is provided an agrochemical formulation formed by dilution with water of the concentrate according to the first aspect, and addition of at least one agrochemical active.

According to a fourth aspect of the present invention there is provided the use of a styrene (meth)acrylic copolymer as a dispersant in an agrochemical concentrate comprising at least one micronutrient.

According to a fifth aspect of the present invention there is provided a method of treating vegetation to control pests, the method comprising applying an agrochemical formulation of the third aspect, either to said vegetation or to the immediate environment of said vegetation.

According to a sixth aspect of the present invention there is provided a method of forming an agrochemical formulation comprising the steps of;
   preparing an active formulation comprising at least one agrochemical active diluted in water; and
   adding a micronutrient concentrate in accordance with either the first aspect or the sixth aspect.

It has been found that dispersants which are styrene (meth)acrylic copolymers when used in agrochemical concentrates are able to provide stability and suspensibility of micronutrients, and in particular where the concentration of the micronutrients is high.

As used herein, the terms 'for example' 'for instance' 'such as' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_6$ alkyl'), the number refers to the total number of carbon atoms present in the substituent group, including any present in any branched groups. Additionally, when describing the number of carbon atoms in, for example fatty acids, this refers to the total number of carbon atoms including the one at the carboxylic acid, and any present in any branch groups.

The dispersant of the present invention may be referred to herein as a polymeric dispersant The polymeric dispersant may be a styrene (meth)acrylic acid copolymer. The repeating units in the copolymer are conveniently considered as residues of monomer components. The polymeric dispersant may preferably be water dispersible.

The (meth)acrylic acid monomer(s) can be acrylic acid, methacrylic acid, crotonic acid or a mixture of two or more of these. The (meth)acrylic acid monomer(s) can be or include (meth)acrylic monomers which are derivatives of (meth)acrylic acid which include strong acid, especially sulphate acid or sulphonic acid groups (or their salts). Examples of such monomers include acrylamido methyl propyl sulphonate (AMPS) and (meth)acrylic acid isethionate. When present such strong acid modified monomers usually form from 1 to 30 mol. %, more usually 2 to 20 mol. %, and desirably from 5 to 15 mol. %, of the acrylic acid monomers in the copolymer.

The styrene monomer(s) can be, and desirably is, styrene as such or a substituted styrene particularly a hydrocarbyl, desirably alkyl, substituted styrene, in which the substituent(s) are on the vinyl group or on the aromatic ring of the styrene e.g. α-methyl styrene and vinyl toluene. As with the (meth)acrylic acid monomer, the styrene monomer can be or include styrene monomers including strongly acid, particularly sulphonic acid substituents. When present such strong acid modified monomers usually form from 1 to 30 mol. %, more usually 2 to 20 mol. %, and desirably from 5 to 15 mol. %, of the styrene monomers in the copolymer.

In the water dispersible styrene (meth)acrylic copolymer used in the invention, the molar ratio of residues of the (meth)acrylic acid monomer(s) to those of the styrene monomer(s) is generally from 20:1 to 1:5, more usually 10:1 to 1:2 and particularly from 3:1 to 1:1. Generally correspondingly, the proportions of residues of the monomers by weight are typically from 93 wt. % to 10 wt. %, more usually 87 wt. % to 25 wt. %, particularly 67 wt. % to 40 wt. %, of the (meth)acrylic acid monomer(s) and from 7 wt. % to 90 wt. %, more usually 13 wt. % to 75 wt. %, particularly 33 wt. % to 60 wt. %, of the styrene monomer(s).

Other monomers, such as acidic monomers e.g. itaconic acid or maleic acid or anhydride; strongly acidic monomers such as methallyl sulphonic acid (or a salt); or non-acidic acrylic monomers e.g. acrylic esters which may be alkyl esters particularly $C_1$ to $C_6$ alkyl esters such as methyl methacrylate, butyl methacrylate or butyl acrylate or hydroxy alkyl esters particularly $C_1$ to $C_6$ hydroxyalkyl esters such as hydroxy ethyl methacrylate, or hydroxy propyl methacrylate; or vinyl monomers such as vinyl acetate, can be included. Typically, the proportion of such other monomer(s) will be not more than about 25 mol. %, usually not more than about 15 mol. %, more usually not more than about 5 mol. %, of the total monomers used. The proportion by weight of other monomers will typically be not more than about 30 wt. %, usually not more than about 20 wt. %, more usually not more than about 10 wt. %.

The polymeric dispersant can be a single styrene acrylic acid copolymer or a blend including two or more such copolymers. In particular, when strong acid residues are included in the polymeric dispersant, the dispersant can be a blend of copolymer including strong acid residues and copolymer not including such residues. In such blends, it is generally desirable that the ratio of such copolymers is from 1:10 to 10:1, more usually 5:1 to 1:5, by weight. In particular, the proportion of copolymer including strong acid residues is desirably at least 25%, more usually at least 40%, by weight of the polymeric dispersant.

When strong acid residues are included in the polymeric dispersant, the overall proportion of monomer residues including strong acid groups is desirably from 0.25 mol. % to 25 mol. %, more usually from 0.5 mol. % to 20 mol. % and desirably from 1 mol. % to 10 mol. %.

The inclusion of monomers having strongly acidic substituent groups in the polymeric dispersant can provide improved dispersion of the solid granular form of the agrochemical formulations when dispersed in hard water, particularly water having a hardness above 500 ppm e.g. up to 1,000 ppm, up to 2,000 ppm or even up to 5,000 ppm.

The polymeric dispersant desirably has a molecular weight of from 750 to 20,000, more desirably from 1,000 to 10,000 and particularly from 1,500 to 5,000.

The polymeric dispersant can be used as the free acid or as a salt. In practice, the form present in a formulation will be determined by the acidity of the formulation. Desirably, the formulation will be near neutral and so most of the acid groups will be present as salts. The cations in any such salt can be alkali metal, particularly sodium and/or potassium, ammonium, or amine, including alkanolamine such as ethanolamine, particularly tri-ethanolamine.

Polymeric dispersants used in this invention are desirably free from solvent which might interfere with the micronutrient or cause the granules to stick together. Also it is useful if the polymeric dispersant can be used satisfactorily in a variety of different granulation processes. Further desirably the polymeric dispersant is heat stable, and non-gelling.

To aid dispersion of the micronutrient component(s) in the spray formulation after dilution with water, it is desirable that the polymeric dispersant is compatible with and more usually interacts strongly with, the surface of any water insoluble micronutrient present in the formulation. Water insoluble micronutrients may be used as powders, absorbed/adsorbed onto solid support material or in microencapsulated form. Where microencapsulated micronutrients are used the polymeric dispersant is also desirably compatible with common shell wall materials used in such microcapsules e.g. polyurea, polyurethane, polyester, polycarbonate, polysulphonamide and polyamide.

The dispersing agent used in the formulation of the invention may be wholly of styrene (meth)acrylic copolymers or it may include other dispersant materials such as the conventional dispersants mentioned above, such as naphthalene sulphonate formaldehyde condensates, lignosulphonates, maleic anhydride copolymers and condensed phenolsulphonic acid and their salts. When used in such combinations the weight ratio of styrene (meth)acrylic copolymer(s) to such conventional dispersants will usually be 16 to 2:1 respectively, and more usually 12 to 4:1, particularly from 10 to 6:1.

Other conventional dispersants and dispersing aids such as polyvinylpyrrolidone (PVP), polyvinyl alcohol (PVOH), phosphate esters such as the tristeryl phenol based phosphate esters available as Soprofor FL, carbomethoxycellulose (CMC), starch, alginate, gum arabic, sorbitol, and sucrose (as mentioned above) can be included.

When used such conventional materials are typically used as minor components of the dispersing agent e.g. at from 1 wt. % to 20 wt. % of the total dispersant.

The dispersant of the present invention will typically be used in an amount proportional to the amount of the micronutrient in the concentrate. Typically, the concentration of the dispersant in such a concentrate will be from 0.2 wt. % to 50 wt. %. Preferably, from 0.4 wt. % to 30 wt. %. More preferably, from 0.5 wt. % to 20 wt. %. Further preferably, from 0.5 wt. % to 10 wt. %. Most preferably, from 1.0 wt. % to 8 wt. %.

The polymeric dispersants can be made by free radical initiated polymerisation, e.g. using a peroxide or a redox initiator, particularly by solution polymerisation, of the constituent monomers, optionally also with a chain transfer agent such as an alkyl mercaptan which acts to control the molecular weight of the polymer. Suitable methods are described for example in EP 0697422.

The concentrate may additionally comprise a wetting agent or agents. Wetting agents may be included in the concentrate to speed up dispersion of the micronutrient, and to enhance the wetting of plant leaves by the spray once the concentrate is diluted for use.

Suitable wetting agents may be selected from non-ionic surfactants. In particular, wetting agents may be selected from alcohol ethoxylates e.g. $C_9$ to $C_{15}$, particularly primary, alcohols, which may be linear or branched, particularly mono-branched, ethoxylates with from 5 to 30 moles of ethylene oxide; and alkoxylates of such alcohols particularly mixed ethoxylate/propoxylates which may be block or random mixed alkoxylates, typically containing from 3 to 10 ethylene oxide residues and from 1 to 5 propylene oxide residues, particularly where the polyalkoxylate chain is terminated with propylene oxide unit(s); polyoxyethylene/polyoxypropylene copolymers, particularly block copolymers, such as the Synperonic PE series of copolymers and Atlas G 5000 available from Uniqema, and alkyl polysaccharides; anionic surfactants e.g. isethionates, such as sodium cocoyl isethionate, naphthalene sulphonic acids or sulphosuccinates. Mixtures of such wetting agents can also be used.

Suitable non-ionic alkoxylates having particular utility as wetting agents in the context of the present invention may be selected from lauryl alcohol (4 EO) ethoxylate, lauryl alcohol (5 EO) ethoxylate, lauryl alcohol (6 EO) ethoxylate, oleyl (3 EO) ethoxylate, oleyl (5 EO) ethoxylate, or oleyl (10 EO) ethoxylate.

The non-ionic alkoxylates may in particular be selected from those which are miscible with the dispersant.

Typically, the amount of the wetting agent in the concentrate will be from 0.2 wt. % to 50 wt. %. Preferably, from 0.4 wt. % to 30 wt. %. More preferably, from 0.5 wt. % to 20 wt. %. Further preferably, from 0.5 wt. % to 10 wt. %. Most preferably, from 1.0 wt. % to 8 wt. %.

The concentrate comprises at least one micronutrient. In such concentrates the micronutrient is typically in a dry form.

Nutrients refer to chemical elements and compounds which are desired or necessary to promote or improve plant growth. Nutrients generally may be described as macronutrients or micronutrients. Suitable nutrients for use in the concentrates according to the invention are micronutrients, preferably those which are solid at room temperature or are partially soluble in water.

Micronutrients typically refer to trace metals or trace elements, and are often applied in low doses. Suitable micronutrients include trace elements selected from zinc, boron, chlorine, copper, iron, molybdenum, and manganese. It is envisaged that the dispersant of the present invention would have broad applicability to all types of micronutrients.

The micronutrients may be in a soluble form or included as insoluble solids, and may in the form of salts or chelates. Preferably, the micronutrient is in the form of a carbonate or oxide.

Preferably, the micronutrient may be selected from zinc, calcium, molybdenum or manganese, or magnesium. Most preferably manganese.

The micronutrient may preferably be present in salt form. Particularly preferred micronutrients for use with the present invention may be selected from zinc oxide, manganese carbonate, manganese oxide, or calcium carbonate.

The amount of micronutrient in the concentrate may be at least 40 wt. %, more usually at least 50 wt. %, particularly at least 55 wt. % by weight. This is based on the amount of solid micronutrient in the total concentrate.

The particle size of the particles of or including micronutrients in the concentrate should be small enough that there is no practical risk of blocking spray jets.

Typically, as mixed into formulations during make up the average particle size of solid micronutrients is from 50 μm to 100 μm, but formulations are typically wet milled after mixing to reduce the average particle size to from 1 μm to 10 μm, more preferably from 1 μm to 5 μm.

The use of dispersants is in part to avoid agglomeration of the particles of or including micronutrients during storage and use.

The concentrate of the present invention may also comprise at least one macronutrient. Macronutrients typically refer to those comprising nitrogen, phosphorus, and potassium, and include fertilisers such as ammonium sulphate, and water conditioning agents. Suitable macronutrients include fertilisers and other nitrogen, phosphorus, or sulphur containing compounds, and water conditioning agents.

Suitable fertilisers include inorganic fertilisers that provide nutrients such as nitrogen, phosphorus, potassium or sulphur. Examples of such fertilisers include:

for nitrogen as the nutrient: nitrates and or ammonium salts such as ammonium nitrate, including in combination with urea e.g. as uran type materials, calcium ammonium nitrate, ammonium sulphate nitrate, ammonium phosphates, particularly mono-ammonium phosphate, di-ammonium phosphate and ammonium polyphosphate, ammonium sulphate, and the less commonly used calcium nitrate, sodium nitrate, potassium nitrate and ammonium chloride;

for phosphorus as the nutrient: acidic forms of phosphorus such as phosphoric, pyrophosphoric or polyphosphoric acids, but more usually salt forms such as ammonium phosphates, particularly mono-ammonium phosphate, di-ammonium phosphate, and ammonium polyphosphate, potassium phosphates, particularly potassium dihydrogen phosphate and potassium polyphosphate;

for sulphur as the nutrient: ammonium sulphate and potassium sulphate, e.g. the mixed sulphate with magnesium.

It will be understood that term 'agrochemical concentrate' refers to a concentrated composition designed to be diluted with water (or a water based liquid) to form the corresponding spray formulations prior to application. The actual concentration of the agrochemical in the concentrate will depend on the nature of the micronutrient and the desired concentration of the micronutrient as diluted in the spray tank.

The concentrate may preferably not comprise any agrochemical active. In such an embodiment, and active would be added later in the spray formulation.

The concentrate may also comprise water in the amount from 10 to 70 wt. %. Preferably, in the amount from 20 to 60 wt. %. Most preferably, from 25 wt. % to 50 wt. %.

The concentrate may be formulated as an emulsifiable concentrate (EC), emulsion concentrate (EW), suspension concentrate (SC), soluble liquid (SL), as an oil-based suspension concentrate (OD), and/or suspoemulsions (SE).

In an EC formulation and in an SL formulation, the micronutrient may be present in dissolved form, whereas in an OD, SC, EW, or SE formulations the active compound may be present as a solid or emulsified liquid.

It is envisaged that the adjuvant of the present invention will particularly find use in a EC, EW, SC, OD, or SE formulation, and most preferably SC.

Agrochemically active compounds, including insecticides and fungicides, require a formulation which allows the active compounds to be taken up by the plant/the target organisms.

The term 'agrochemical formulation' as used herein refers to compositions including an active agrochemical, and is intended to include all forms of compositions, including diluted concentrates and spray formulations. If not specifically stated, the agrochemical formulation of the present invention may be in the form of a diluted concentrate, or a sprayable formulation.

Spray formulations are aqueous agrochemical formulations including all the components which it is desired to apply to the plants or their environment. Spray formulations can be made up by simple dilution of concentrates containing desired components (other than water), or by mixing of the individual components, or a combination of diluting a concentrate and adding further individual components or mixtures of components. Typically such end use mixing is carried out in the tank from which the formulation is sprayed, or alternatively in a holding tank for filling the spray tank. Such mixing and mixtures are typically termed tank mixing and tank mixtures.

The agrochemical active may therefore be incorporated into the formulation of the after dilution of the concentrated formulation of the spray liquor (tank-mix).

According to the needs of the customer, said concentrates may be diluted for use resulting in a dilute composition and the agrochemical active added. The resulting agrochemical active concentration in the diluted concentrate (the formulation) may be about 0.5 wt. % to about 1 wt. %. In said dilute composition (for example, a spray formulation, where a spray application rate may be from 10 to 500 $l\cdot ha^{-1}$) the agrochemical active concentration may be in the range from about 0.001 wt. % to about 1 wt. % of the total formulation as sprayed.

The dispersant of the present invention will typically be used in an amount proportional to the amount of the micronutrient in the concentrate, and therefore this ratio may remain the same once the dilute spray formulation is formed.

Upon dilution of the concentrate to form, for example, a spray formulation, the dispersant will typically be present in the dilute formulation at a concentration of from 0.01 wt. % to 2 wt. %, more usually from 0.03 wt. % to 0.5 wt. % of the spray formulation. Further preferably, from 0.12 wt. % to 0.4 wt. % of the spray formulation.

The ratio of dispersant to micronutrient in the agrochemical formulation is preferably from about 0.1:1 to about 1:1 respectively. More preferably, from about 0.3:1 to about 0.8:1.

The ratio of dispersant to active agrochemical in the agrochemical formulation is preferably from about 0.1:1 to about 1:1 respectively. More preferably, from about 0.3:1 to about 0.8:1.

When concentrates are used, the concentrates will typically be diluted to form the spray formulations. The dilution may be with from 1 to 10,000, particularly 10 to 1,000, times the total weight of the concentrate of water to form the spray formulation.

Where an agrochemical active is present in the aqueous end use formulation as solid particles, most usually it will be present as particles mainly of active agrochemical. However, if desired, the active agrochemical can be supported on a solid carrier e.g. silica or diatomaceous earth, which can be solid support, filler or diluent material as mentioned above.

The spray formulations will typically have a pH within the range from moderately acidic (e.g. about 3) to moderately alkaline (e.g. about 10), and particular near neutral (e.g. about 5 to 8). More concentrated formulations will have similar degrees of acidity/alkalinity, but as they may be largely non-aqueous, pH is not necessarily an appropriate measure of this.

The agrochemical formulation may include solvents (other than water) such as monopropylene glycol, oils which can be vegetable or mineral oils such as spray oils (oils included in spray formulations as non-surfactant adjuvants), associated with the first and co-adjuvants. Such solvents may be included as a solvent for the adjuvant, and/or as a humectant, e.g. especially propylene glycol. When used such solvents will typically be included in an amount of from 5 wt. % to 500 wt. %, desirably 10 wt. % to 100 wt. %, by weight of the adjuvant. Such combinations can also include salts such as ammonium chloride and/or sodium benzoate, and/or urea especially as gel inhibition aids.

The agrochemical formulation may also include other components as desired. These other components may be selected from those including:

binders, particularly binders which are readily water soluble to give low viscosity solutions at high binder concentrations, such as polyvinylpyrrolidone; polyvinyl alcohol; carboxymethyl cellulose; gum arabic; sugars e.g. sucrose or sorbitol; starch; ethylene-vinyl acetate copolymers, sucrose and alginates, diluents, absorbents or carriers such as carbon black; talc; diatomaceous earth; kaolin; aluminium, calcium or magnesium stearate; sodium tripolyphosphate; sodium tetraborate; sodium sulphate; sodium, aluminium and mixed sodium-aluminium silicates; and sodium benzoate, disintegration agents, such as surfactants, materials that swell in water, for example carboxy methylcellulose, collodion, polyvinylpyrrolidone and microcrystalline cellulose swelling agents; salts such as sodium or potassium acetate, sodium carbonate, bicarbonate or sesquicarbonate, ammonium sulphate and dipotassium hydrogen phosphate;

wetting agents such as alcohol ethoxylate and alcohol ethoxylate/propoxylate wetting agents;

dispersants such as sulphonated naphthalene formaldehyde condensates and acrylic copolymers such as the comb copolymer having capped polyethylene glycol side chains on a polyacrylic backbone;

emulsifiers such as alcohol ethoxylates, ABA block co polymers, or castor oil ethoxylates;

antifoam agents, e.g. polysiloxane antifoam agents, typically in amounts of 0.005 wt. % to 10 wt. % of the formulation;

viscosity modifiers such as commercially available water soluble or miscible gums, e.g. xanthan gums, and/or cellulosics, e.g. carboxy-methyl, ethyl or propylcellulose; and/or preservatives and/or anti-microbials such as organic acids, or their esters or salts such as ascorbic e.g. ascorbyl palmitate, sorbic e.g. potassium sorbate, benzoic e.g. benzoic acid and methyl and propyl 4-hydroxybenzoate, propionic e.g. sodium propionate, phenol e.g. sodium 2-phenylphenate; 1,2-benzisothiazolin-3-one; or formaldehyde as such or as paraformaldehyde; or inorganic materials such as sulphurous acid and its salts, typically in amounts of 0.01 wt. % to 1 wt. % of the formulation.

Adjuvants, such as surfactant adjuvants, may be included in the concentrate and formulations of this invention. An adjuvant is generally defined as a chemical or a mixture of chemicals (commonly surfactants) capable of improving the biological activity or effectiveness of an agrochemical active. Adjuvants do not themselves control or kill pests. Instead, these additives modify some property (e.g. spreading, retention, penetration, droplet size etc.) of the agrochemical formulation which improves the ability of the active to penetrate, target, or protect the target organism. The typical types of compounds used as adjuvants may include surfactants, emulsifiers, oils, and salts. Adjuvants do not significantly inhibit translocation of the active in the treated plant. In addition, the adjuvant should not produce unwanted phytotoxic effects on the plant.

The agrochemical formulation can include adjuvants, particularly surfactant adjuvants, especially non-ionic surfactants, such as alcohol alkoxylates e.g. ethoxylates, particularly of $C_8$ to $C_{18}$ alcohols which can be linear, branched or linear/branched mixtures; alkylamine alkoxylates e.g. ethoxylates, particularly of $C_8$ to $C_{18}$ alkylamines; sorbitol and sorbitan fatty acid, particularly $C_8$ to $C_{18}$ fatty acid, esters and their ethoxylated derivatives; and alkyl, particularly $C_6$ to $C_{14}$ alkyl, polysaccharides. Examples include alkylpolysaccharides (more properly called alkyl oligosaccharides); fatty amine ethoxylates e.g. coconut alkyl amine 2EO; and derivatives of alk(en)yl succinic anhydride, in particular those described in PCT applications WO 94/00508 and WO 96/16930.

The adjuvant can be included in the formulation or adsorbed in or adsorbed on a solid support e.g. silica or diatomaceous earth, which can be solid support, filler or diluent material as mentioned above.

The agrochemical active included in the formulation may preferably be a solid phase agrochemical active. Solid agrochemical active compounds are to be understood in the present composition as meaning all substances customary for plant treatment, whose melting point is above 20° C. (standard pressure). Solid agrochemical actives will also include insoluble active ingredients, i.e. active ingredients whose solubility in water is such that a significant solid content exists in the formulation after addition.

Agrochemical actives refer to biocides which, in the context of the present invention, are plant protection agents, more particular chemical substances capable of killing different forms of living organisms used in fields such as medicine, agriculture, forestry, and mosquito control. Also counted under the group of biocides are so-called plant growth regulators.

Biocides for use in agrochemical formulations of the present invention are typically divided into two sub-groups:
pesticides, including fungicides, herbicides, insecticides, algicides, moluscicides, miticides and rodenticides, and
antimicrobials, including germicides, antibiotics, antibacterials, antivirals, antifungals, antiprotozoals and antiparasites.

In particular, biocides selected from insecticides, fungicides, or herbicides may be particularly preferred.

The term 'pesticide' will be understood to refer to any substance or mixture of substances intended for preventing, destroying, repelling, or mitigating any pest. A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given.

A fungicide is a chemical control of fungi. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies.

Examples for suitable fungicides, according to the present invention, encompass the following species: (3-ethoxypropyl)mercury bromide, 2-methoxyethylmercury chloride, 2-phenylphenol, 8-hydroxyquinoline sulphate, 8-phenylmercuri oxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulphide, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulphide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper (II) carbonate, basic, copper fungicides, copper hydroxide, copper naphthenate, copper oleate, copper oxychloride, copper(II) sulphate, copper sulphate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulphon, dinoterbon, diphenylamine, dipyrithione, disulphiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulph, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, fluopicolide, fluoroimide, fluotrimazole, fluoxastrobin, fluquinconazole, flusilazole, flusulphamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulphocarb, methfuroxam, methyl bromide, methyl isothiocyanate, methylmercury benzoate, methylmercury dicyandiamide, methylmercury pentachlorophenoxide, metiram, metominostrobin, metrafenone, metsulphovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulphamide fungicides, phosdiphen, phthalide, phthalimide fungicides, picoxystrobin, piperalin, polycarbamate, polymeric dithiocarbamate fungicides, polyoxins, polyoxorim, polysulphide fungicides, potassium azide, potassium polysulphide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfiir, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulphide, spiroxamine, streptomycin, strobilurin fungicides, sulphonanilide fungicides, sulphur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide, and mixtures thereof.

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are non-selective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat.

Suitable herbicides may be selected from the group comprising: aryloxycarboxylic acid e.g. MCPA, aryloxyphenoxypropionates e.g. clodinafop, cyclohexanedione oximes e.g. sethoxydim, dinitroanilines e.g. trifluralin, diphenyl ethers e.g. oxyfluorfen, hydroxybenzonitriles e.g. bromoxynil, sulphonylureas e.g. nicosulphuron, triazolopyrimidines e.g. penoxsulam, triketiones e.g. mesotriones, or ureas e.g. diuron.

Particularly preferred herbicides may be selected from 2,4-dichlorophenoxyacetic acid (2,4-D), atrazine, dicamba as benzoic acid, glyphosate, imazapic as imidazolinone, metolachlor as chloroacetamide, picloram, clopyralid, and triclopyr as pyridinecarboxylic acids or synthetic auxins.

An insecticide is a pesticide used against insects in all developmental forms, and includes ovicides and larvicides used against the eggs and larvae of insects. Insecticides are used in agriculture, medicine, industry and the household.

Suitable insecticides may include those selected from:
Chlorinated insecticides such as, for example, Camphechlor, DDT, Hexachloro-cyclohexane, gamma-Hexachlorocyclohexane, Methoxychlor, Pentachlorophenol, TDE, Aldrin, Chlordane, Chlordecone, Dieldrin, Endosulphan, Endrin, Heptachlor, Mirex and their mixtures;

Organophosphorous compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulphoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphos-methyl, Profenofos, Terbufos, Tetrachlorvinphos, Tribufos, Trichlorfon and their mixture;

Carbamates such as, for example, Aldicarb, Carbofuran, Carbaryl, Methomyl, 2-(1-Methylpropyl)phenyl methylcarbamate and their mixtures;

Pyrethroids such as, for example, Allethrin, Bifenthrin, Deltamethrin, Permethrin, Resmethrin, Sumithrin, Tetramethrin, Tralomethrin, Transfluthrin and their mixtures;

Plant toxin derived compounds such as, for example, Derris (rotenone), Pyrethrum, Neem (Azadirachtin), Nicotine, Caffeine and their mixtures.

Neonicotinoids such as imidacloprid.

Abamectin e.g. emamactin

Oxadiazines such as indoxacarb

Anthranilic diamides such as rynaxypyr

Rodenticides are a category of pest control chemicals intended to kill rodents. Suitable rodenticides may include anticoagulants, metal phosphides, phosphides, and calciferols (vitamins D), and derivatives thereof.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulphate. A nematicide is a type of chemical pesticide used to kill parasitic nematodes (a phylum of worm).

In the following examples, antimicrobials suitable for agrochemical compositions according to the present invention are given.

Bactericidal disinfectants may include those selected from active chlorines, active oxygen, iodine, concentrated alcohols, phenolic substances, cationic surfactants, strong oxidisers, heavy metals and their salts, and concentrated strong acids and alkalis between pH of from 1 to 13.

Suitable antiseptics (i.e., germicide agents that can be used on human or animal body, skin, mucoses, wounds and the like) may include diluted chlorine preparations, iodine preparations, peroxides, alcohols with or without antiseptic additives, weak organic acids, phenolic compounds, and cation-active compounds.

Particular preference is given to active compounds from the classes of the azole fungicides (azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidol, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforin, triticonazole, uniconazole, voriconazole, viniconazole), strobilurin fungicides (azoxystrobin, dimoxystrobin, fluoxastrobin, kresoxim-methyl, metominostrobin, orysastrobin, picoxystrobin, pyraclostrobin, trifloxystrobin), the SDH fungicides, the chloronicotinyl insecticides (clothianidin, dinotefuran, imidacloprid, thiamethoxam, nitenpyram, nithiazin, acetamiprid, nitenpyram, thiacloprid), the insecticidal ketoenols (spirodiclofen, spiromesifen, spirotetramate), fiproles (fiprole, ethiprole) and butenolides, and also pymetrozine, fluopicolid, N-(3',4'-dichloro-5-fluoro-1,1'-biphenyl-2-yl)-3-(difluoromethyl)-1-methyl-1H-pyrazole-4-carboxamide and N-{2-[3-chloro-5-(trifluoromethyl)-2-pyridinyl]ethyl}-2-(trifluoromethyl)benzamide. Particular preference is also given to herbicides, in particular sulphonylureas, triketones and herbicidal ketoenols, and also safeners.

Preferred examples of agrochemical actives may be selected from;
the fungicides tebuconazole, prothioconazole, N-(3',4'-dichloro-5-fluoro-1,1'-biphenyl-2-yl)-3-(difluoromethyl)-1-methyl-1H-pyrazole-4-carboxamide (known from WO 03/070705), N-{2-[3-chloro-5-(trifluoromethyl)-2-pyridinyl]ethyl}-2-(trifluoromethyl)benzamide (known from WO 04/16088), trifloxystrobin, fluopicolid, azoxystrobin;
the insecticides imidacloprid, thiamethoxam, clothianidin, thiacloprid, spirotetramate, fipronil, ethiprol, carbaryl, cypermethrin;
the herbicides 2,4-dichlorophenoxyacetic acid (2,4-D), atrazine, dicamba as benzoic acid, glyphosate, imazapic as imidazolinone, metolachlor as chloroacetamide, picloram, clopyralid, and triclopyr as pyridinecarboxylic acids or synthetic auxins.

Particularly preferred agrochemical actives are those which are high electrolyte actives, and which would otherwise cause instability to the tank mixture when present with the micronutrient dispersion. A particularly preferred example of an agrochemical active is glyphosate.

The concentration of the agrochemical active in the dilute formulation is not critical for the purposes of the present invention, and may be determined by other factors as required. The concentration of the agrochemical active is preferably in the range from 50 g/l to 500 g/l. More preferably, in the range from 75 g/l to 250 g/l. Most preferably, in the range from 90 g/l to 180 g/l.

The agrochemical spray formulation may be formed as desired, but typically is formed by firstly preparing an active formulation comprising at least one agrochemical active diluted in water, this may be from an active concentrate or simply active added to water, and adding a micronutrient concentrate in accordance with either the first aspect or the sixth aspect.

The invention further includes a method of treating plants using formulations including at least one micronutrient and the dispersant of the first aspect, and an agrochemical active.

Accordingly the invention further includes methods of use including:
a method of providing micronutrients to vegetation by applying to the vegetation, or the immediate environment of the vegetation e.g. the soil around the vegetation, a spray formulation including at least one dispersed phase micronutrient and the dispersant of the first aspect; and/or
a method of providing micronutrients, and killing or inhibiting vegetation by applying to the vegetation, or the immediate environment of the vegetation e.g. the soil around the vegetation, a spray formulation including at least one dispersed phase micronutrient and the dispersant of the first aspect, and an agrochemical active which is one or more pesticides, for example insecticides, fungicides, or acaricides.

The use of the dispersants of the present invention has been found to provide for micronutrient concentrates which are stable. Additionally, the micronutrient may be formed by milling/grinding and the presence of the dispersant provides for reduced formation of gel blocks during the process.

The dispersant has also been found to allow for preparation of stable micronutrient concentrates which are able to comprise relatively high amounts of micronutrients whilst remaining stable, and therefore having an improved shelf life.

Additionally, use of the dispersant in the micronutrient concentrate has been found to provide stability to end use spray formulations prepared from the concentrate and comprising an agrochemical active, especially a high electrolyte agrochemical active. This stability in particular may be observed as a reduction in the levels of flocculation/coalescence in the spray formulation.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 25° C.), unless otherwise stated herein, or unless otherwise stated in the referenced test methods and procedures.

The following test methods were used to determine performance of the adjuvant compositions.
Particle size values—the $D(v,0.5)$ and $D(v,0.9)$ values were determined by dynamic light scattering analysis using a Malvern Mastersizer 2000 with a Hydro 2000SM attachment running on water set at 2,100 rpm. The refractive index of the material was set as 1.53 with an absorbance of 0.1. 12,000 snaps were taken over 12 seconds to obtain the data. An average of three runs was used to determine a final particle size. From the particle size values obtained, $D(v,0.5)$ and $D(v,0.9)$ values were readily determined.
Suspensibility—Sample was diluted in 342 ppm hard water with 5 ml of concentrate and 95 ml of water. 40 ml of 342 ppm $Ca^{2+}$ water was placed in 100 ml stoppered measuring cylinder. 5 ml of the formulation was added and topped up to 100 ml mark with 342 $Ca^{2+}$ ppm water (mimicking a 20 fold dilution upon application). The sample was inverted 30 times and left to stand for 30 minutes. The top 90% of the suspension was removed by using a vacuum pump connected to a catch pot. The 90% was then dried to constant weight at 50° C. overnight in an evaporating dish. The suspensibility was calculated using the weight of the solid material obtained.
Stability—The stability of all the formulations was assessed after the stated time period at room temperature (RT) and 54° C. The samples were tested in a Turbiscan to measure any sedimentation/creaming that may have occurred.
Compounds as used in the following examples are identified as follows:
$MnCO_3$—manganese carbonate tech. 87.7%
Antiprex A—existing polymeric dispersants/rheology modifiers (available from BASF)
DS1—styrene acrylic acid copolymer (solid) dispersant of invention
DS2—styrene acrylic acid copolymer (liquid) dispersant of invention Atlox AL2575—glyphosate adjuvant of $C_8$-$C_{10}$ alkylpolysaccharide (from Croda International)
Multitrope 1214—biodegradable surfactant, based on the phosphate ester of a natural fatty acid (from Croda International)
Atlas G-5002L—butyl block copolymer emulsifier (from Croda International)
Atlox 4894—alcohol alkoxylate surfactant blend (from Croda International)
Synperonic A7—nonionic wetting agent polyoxyethylene (7) $C_{12}$-$C_{15}$ alcohol (from Croda International)
Atlox AL-3772—silicone emulsion used as antifoam (from Croda International)
Xantham gum—thickener
Optasense RMA52—anionic rheology modifier of sodium polyacrylate and paraffinum liquidum and trideceth-6 (from Croda International)
Mn dis—aqueous suspension of manganese carbonate with existing polyacrylate dispersant Concentrate Example Formulations Several example formulations of the invention were prepared. Table 1 shows the example formulations prepared.

TABLE 1

Example concentrate formulations (values expressed as wt. %)

| Components | C1 | C2 | C3 | C4 | C5 |
|---|---|---|---|---|---|
| MnCO$_3$ | 52.0 | 52.0 | 65.0 | 65.0 | 65.0 |
| DS1 | 0.5 | 1.0 | 2.0 | — | — |
| DS2 | — | — | — | 5.0 | 5.0 |
| Atlox 4894 | 2 | — | — | — | — |
| Synperonic A7 | — | 0.5 | 0.5 | 0.5 | 0.5 |
| Glycerin | 4 | — | 4 | — | — |
| Atlox AL-3772 | 0.2 | 0.3 | 0.3 | 0.3 | 0.3 |
| Xantham gum | 0.15 | 0.15 | 0.15 | 0.15 | — |
| Preservative | 0.02 | 0.02 | 0.02 | 0.02 | 0.02 |
| Water | 41.1 | 46.0 | 28.0 | 29.0 | 29.2 |

The samples were prepared by first adding to a beaker 70% w/w of total water amount. Then the glycerin, where necessary, was added, then dispersants, humectants and 50% w/w of total Atlox AL-3772 amount. Lastly the manganese carbonate was added. This mixture was then milled.

A separate mixture was prepared with xantham gum, preservative and water (30% w/w of total amount). After adding all components, it was allowed to mix for 1 hour.

Once the manganese carbonate mixture had been sufficiently milled the remaining amount of Atlox AL-3772 was added, and the thickener mixture was added to finish the formulation.

The samples were evaluated according to ABNT methodologies to comply with technical requirements.

Compatibility Tests with Active

The concentrate formulation C5 was tested with glyphosate to ensure compatibility. Evaluation of C5 with glyphosate was done by preparing a dilute formulation as indicated in Table 2.

TABLE 2

Compatibility test with glyphosate

| Components | Volume |
|---|---|
| Glyphosate 360 g/L (a.e.) | 15 mL |
| Micronutrient formulation | 5 mL |
| Water | Made up to 1 L |

The mixture was prepared in a cylinder tube adding first the water amount than the glyphosate mixing to ensure that the mixture was homogeneous. Next was added the micronutrient formulation and the glass bottle was inverted by thirty times and the final aspect visualised. The procedure was executed with the standard sample (Mn dis) which acted as a reference, and with C5.

Typically existing manganese formulations show incompatibility issues when in contact to glyphosate, like clumping or flocculation.

The compatibility test was conducted in the same way as a suspensibility test but instead of running the test in regular water, it was done in a glyphosate "tank-mix" as shown in Table 2.

The standard Mn dis formulation does not open when added to the tank-mix composition, and also went to the bottom of the flask in a few seconds needing vigorous mixing to disperse it. The formulation using C5 opened easily when added to the tank-mix and remained dispersed even without mixing.

The cylinder tubes were inverted around thirty times. After few minutes it was observed that the Mn dis based formulation caused flocculation and the content that should have been dispersed had become decanted. The formulation based on C5 remained as a suspension and no flocculation was observed.

The compatibility tests showed that the formulation based on C5 has a better performance than the existing Mn dis formulation, as also a better compatibility with glyphosate.

Physical Characteristics of C1-C5

Sample was prepared using C5. C5 was evaluated according to ABNT methodologies and the results can be seen on Table 3.

TABLE 3

Physicochemical evaluation of C5

| Parameters evaluated | 24 hours RT | 14 days | | |
|---|---|---|---|---|
| | | 5° C. | RT | 54° C. |
| Visual Aspect | Fluidity | Keeps initial aspect | Keeps initial aspect | Keeps initial aspect |
| Suspensibility (% w/w) | 71 | 69 | 71 | 68 |
| Density (g/mL) | 1.80 | 1.80 | 1.80 | 1.80 |
| D10 (μm) | 0.62 | — | — | — |
| D50 (μm) | 1.74 | — | — | — |
| D90 (μm) | 4.77 | — | — | — |

The results show a fluidity formulation with non-gelling issue and complying with ABNT methodologies.

SUSPENSIBILITY EXAMPLES

Further concentrate formulations were prepared to evaluate suspensibility as shown in Table 4.

TABLE 4

Concentrate formulations (values expressed in wt. %)

| Components | A | C6 | C7 | C8 | C9 | C10 |
|---|---|---|---|---|---|---|
| MnCO$_3$ tech. | 60 | 60 | 60 | 60 | 60 | 60 |
| Antiprex ™ A | — | 5.5 | — | — | — | — |
| DS2 | — | — | 5.5 | 5.5 | 5.5 | — |
| DS1 | — | — | — | — | — | 5.5 |
| Synperonic A7 | — | 0.5 | — | 0.5 | — | 0.5 |

TABLE 4-continued

Concentrate formulations (values expressed in wt. %)

| Components | A | C6 | C7 | C8 | C9 | C10 |
|---|---|---|---|---|---|---|
| AL2575 | — | — | — | — | 0.5 | — |
| Atlox AL-3772 | — | 0.1 | 0.1 | 0.1 | 0.1 | 0.1 |
| Water | — | 33.9 | 34.4 | 33.9 | 33.9 | 33.9 |

A = Mn dis

The prepared concentrate formulations were then assessed for the milling ability, aspect, and tank mix compatibility as previously described above.

TABLE 5

Assessment of C6-C10

| | A | C6 | C7 | C8 | C9 | C10 |
|---|---|---|---|---|---|---|
| Mill Process | NA | Ok | Viscosity increases during mill process | Ok | Ok | Ok |
| Aspect (initial) | FG | FG(M) | FG(M) | FG(M) | FG(M) | FG(M) |
| Tank mix compatibility | + | ++ | +++ | +++ | +++ | +++ |

FG - Forms gels with time. Presence of gel block.
FM - Flows when applying mild force
+ - poor glyphosate tank mix compatibility
++ - acceptable glyphosate tank mix compatibility
+++ - good acceptable glyphosate tank mix compatibility Suspensibility Tests for C8

Concentrate formulation C8 was tested with the reference sample Mn dis. The samples were analysed using a Turbiscan once diluted. The formulations were evaluated for tank mix compatibility using Roundup Transorb (from Monsanto) as a standard sample of glyphosate. The formulations were prepared according to Table 6.

TABLE 6

Formulations prepared for suspensibility analysis

| Components | Volume |
|---|---|
| Glyphosate 360 g/L (a.e.) | 15 mL |
| Manganese formulation | 5 mL |
| Water | Made up to 1 L |

Glyphosate solution was prepared and 40 mL of it was added to the Turbiscan glassware. The formulation was then added directly to Turbiscan tube that was capped, inverted 10 time and set for immediate scan in the equipment. The Turbiscan was programmed to scan the sample at a temperature set for 30° C.

The Turbiscan measures change in particle size and provided a Turbiscan index (TSI) value. TSI sums all the variations detected in the samples in terms of size and/or concentration. The higher the TSI value, the worse is the stability. A lower TSI value indicates less flocculation and less of the micronutrient coming out of the suspension, therefore better stability. The settings are as shown in Table 7.

TABLE 7 settings for Turbiscan

| | Reference sample | C8 (as formulated Table 6) |
|---|---|---|
| Ref scan | 0 s | 0 s |
| Temperature (° C.) | 30.22 | 30.43 |
| Bottom of the cell | 0.80 | 0.80 |
| Meniuscus | 40.13 | 40.07 |

Results from the Turbiscan are set out in Table 8.

TABLE 8

Turbiscan (global) results

| Time (minutes) | C8 (TSI) | Reference (TSI) |
|---|---|---|
| 0.5 | 0.5 | 30.7 |
| 1 | 1.0 | 38.9 |
| 2 | 1.7 | 43.1 |
| 3 | 3.3 | 44.3 |
| 4 | 7.0 | 45.1 |
| 5 | 12.9 | 45.7 |
| 6 | 18.3 | 46.0 |
| 7 | 21.5 | 46.2 |
| 8 | 23.3 | 46.4 |
| 9 | 24.3 | 46.5 |
| 10 | 25.0 | 46.7 |
| 15 | 27.5 | 48.1 |
| 20 | 29.0 | 49.5 |

The Turbiscan data shows better suspensibility for the formulation of the present invention compared to the reference sample across the time period measured.

It is to be understood that the invention is not to be limited to the details of the above embodiments, which are described by way of example only. Many variations are possible.

The invention claimed is:

1. A stable aqueous liquid agrochemical concentrate comprising;
   i) at least one solid micronutrient, wherein the micronutrient is selected from manganese, and salts thereof;
   ii) a dispersant, said dispersant being a styrene (meth) acrylic copolymer;
   wherein the amount of the at least one solid micronutrient suspended in the concentrate is at least 40 wt. %.

2. The concentrate according to claim 1, wherein the dispersant is water dispersible.

3. The concentrate according to claim 1, wherein monomer repeating units in the copolymer are residues of (meth) acrylic acid monomer(s), and styrene monomer(s).

4. The concentrate according to claim 3, where the (meth)acrylic acid monomer(s) is selected from acrylic acid, methacrylic acid, crotonic acid or a mixture of two or more of these, and optionally comprise (meth)acrylic monomers which are derivatives of (meth)acrylic acid which include strong acid.

5. The concentrate according to claim 3, wherein the styrene monomer(s) is styrene or a substituted styrene, and optionally comprise styrene monomers including strongly acid substituents.

6. The concentrate according to claim 3, wherein the molar ratio of residues of the (meth)acrylic acid monomer(s) to those of the styrene monomer(s) is from 20:1 to 1:5 respectively.

7. The concentrate according to claim 1, wherein the concentration of the dispersant in said concentrate is from 0.2 wt. % to 50 wt. %.

8. The concentrate according to claim 1, wherein the concentrate comprises a wetting agent.

9. The concentrate according to claim 8, wherein the wetting agent is a non-ionic alkoxylate selected from lauryl alcohol (4 EO) ethoxylate, lauryl alcohol (5 EO) ethoxylate, lauryl alcohol (6 EO) ethoxylate, oleyl (3 EO) ethoxylate, oleyl (5 EO) ethoxylate, or oleyl (10 EO) ethoxylate.

10. The concentrate according to claim 1, wherein the micronutrient is selected from manganese carbonate or manganese oxide.

11. The concentrate according to claim 1, wherein the concentrate does not comprise any agrochemical active.

12. The concentrate according to claim 1, wherein the concentrate is formulated as an emulsifiable concentrate (EC), emulsion concentrate (EW), suspension concentrate (SC), soluble liquid (SL), as an oil-based suspension concentrate (OD), and/or suspoemulsions (SE).

13. An agrochemical formulation, said formulation formed by dilution with water of the concentrate according to claim 1, and addition of at least one agrochemical active.

14. The formulation according to claim 13, wherein the agrochemical active is a high electrolyte active.

15. The formulation according to claim 13, wherein the agrochemical active is glyphosate.

16. A method of forming an agrochemical formulation comprising the steps of;
preparing an active formulation comprising at least one agrochemical active diluted in water; and
adding the micronutrient concentrate in accordance with claim 1.

17. A method of treating vegetation to control pests, the method comprising applying an agrochemical formulation of claim 13, either to said vegetation or to the immediate environment of said vegetation.

18. A method of preparing stable aqueous liquid agrochemical concentrate, said method comprising mixing;
at least one solid micronutrient, wherein the micronutrient is selected from manganese, and salts thereof;
a dispersant, said dispersant being a styrene (meth)acrylic copolymer;
wherein the amount of the at least one solid micronutrient suspended in the concentrate is at least 40 wt. %.

* * * * *